Nov. 16, 1954 E. S. BOERNER Plant Pat. 1,317
ROSE PLANT
Filed Oct. 6, 1953
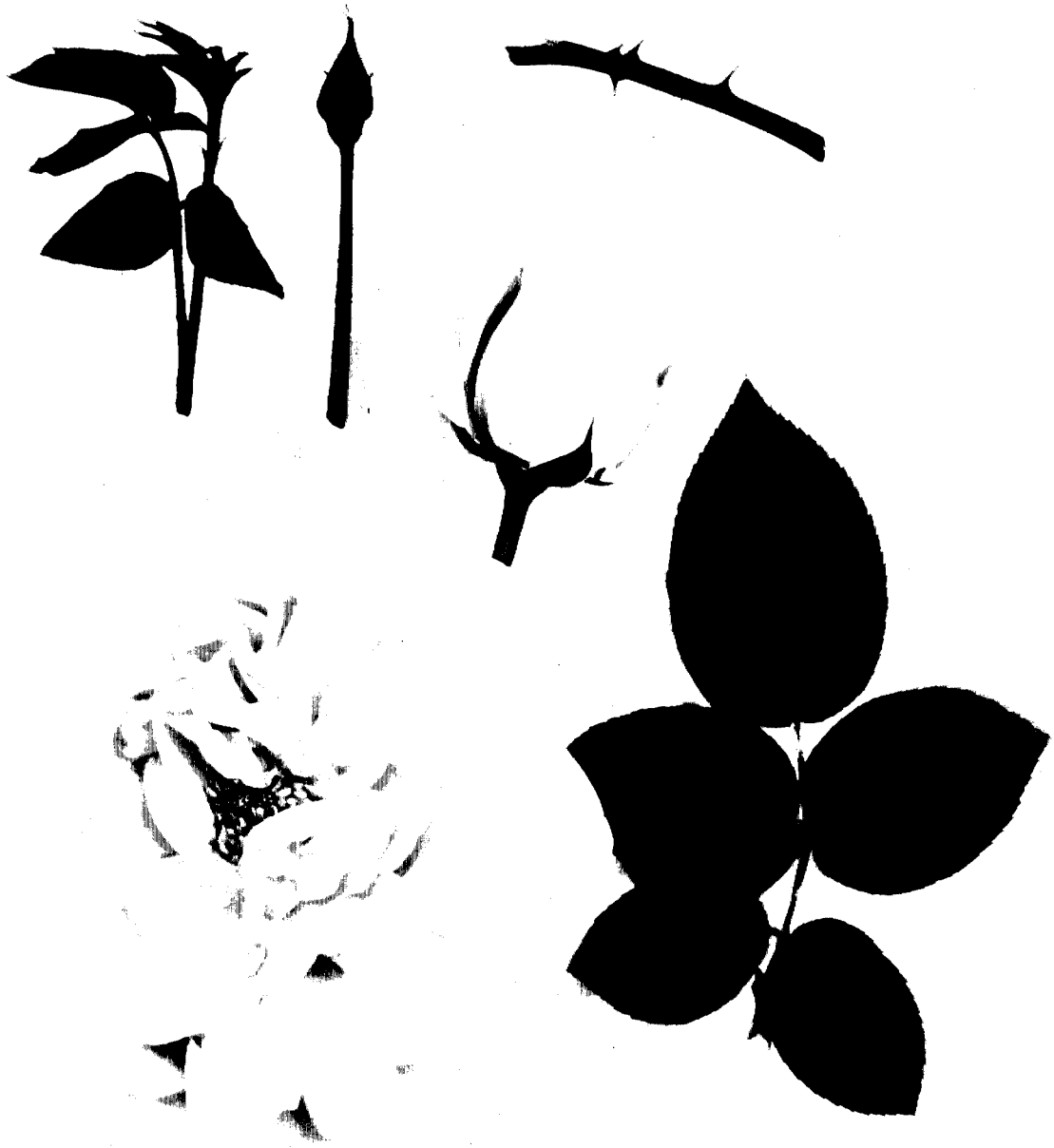
Inventor.
E. S. Boerner
By: Robb & Robb
Attorneys.

United States Patent Office

Plant Pat. 1,317

Patented Nov. 16, 1954

1,317

ROSE PLANT

Eugene S. Boerner, Newark, N. Y., assignor to Jackson & Perkins Company, Newark, N. Y., a corporation of New York Application October 6, 1953, Serial No. 384,533

1 Claim. (Cl. 47—61)

The present invention relates to a new and distinct variety of rose plant of the hybrid tea class, which was originated by me by crossing an unnamed and unpatented seedling of "Break o' Day" (unpatented) × "Golden Rapture" (unpatented) with the variety "Ballet" (Plant Patent No. 800).

The primary objective in making this cross was to obtain a new variety of rose plant having flowers comparable in beauty and form to those of the variety "Ballet," but the plant of which cross is healthier and more disease resistant than the average plants of this parent variety. Accordingly, the seed parent was chosen for its excellence of plant and leaf formation, and the pollen of "Ballet" was applied thereto and resulted in obtaining a stronger plant with more disease resistant foliage in the new variety, yet preserving the general color and form of the flowers of "Ballet" in the new variety, thereby distinguishing the new variety from its parents, as well as from all other varieties of its class.

In addition to the foregoing characteristics, the new variety has an unusual freedom of growth, especially in the greenhouse, and the new variety has been found to be more resistant to fumigant injury to which the variety "Ballet" and many other varieties are commonly subject.

Asexual reproduction of the new variety by budding at Newark, New York, and at Pleasanton, California, shows that the foregoing characteristics and distinctions come true to form and are established and transmitted through succeeding propagations.

The accompanying illustration shows typical specimens of the flowers, foliage and stems of the new variety in different stages of development, with the colors thereof depicted as nearly true as it is reasonably possible to make the same in a color illustration of this character.

The following is a detailed description of my new variety, with color terminology in accordance with Ridgway's Color Standards and Nomenclature:

Parentage: Seedling.
- *Seed parent.*—An unnamed seedling of "Break o' Day" × "Golden Rapture."
- *Pollen parent.*—"Ballet."

Classification:
- *Botanic.*—Hybrid tea.
- *Commercial.*—Hybrid tea.

FLOWER (Observations made from specimens grown in a field at Newark, New York, in the latter part of the month of June, in the late morning.)

Blooming habit: Recurrent—continuous.

Bud:
- *Size.*—Large.
- *Form.*—Ovoid; is not affected by wet or hot weather.
- Color.—When sepals first divide—Carrot Red, Plate 14. When petals begin to unfurl—Grenadine Pink, Plate 2. When half blown: Inside of petals—Bittersweet Pink, Plate 2, lightly overcast with Geranium Pink, Plate 1; reverse of petals—Apricot Yellow, Plate 4, lightly overcast with Light Salmon Orange, Plate 2 at the outer edge of the petal.
- *Sepals.*—Slightly branched; curl back when petals begin to unfurl. Color: inside—Kildare Green, Plate 31; outside—Light Cress Green, Plate 31.
- *Calyx.* — Size — broad. Shape — apple. Aspect — smooth. Color—Parrot Green, Plate 6. Odor when rubbed—none.
- *Peduncle.* — Length — medium. Aspect — smooth. Strength — stiff; heavy. Color — Cosse Green, Plate 5.
- *Opening.*—Opens up well; is not affected by adverse weather conditions.

Bloom:
- *Size.*—Large; average size when fully expanded—4½ to 5 inches.
- *Borne.*—Singly.
- *Stems.*—Medium length; normal strength.
- *Form (when first open).*—High center. Permanence—Retains its form to the end.
- *Petalage.*—Double (full but open center). Number of petals under normal conditions—35 to 40.
- *Color.*—Center of flower—Grenadine Pink, Plate 2. Outer petals—Capucine Buff, Plate 3, lightly overcast with Orient Pink, Plate 2. Base of petals (aiglet)—Lemon Yellow, Plate 4. Inside of petals—Light Salmon Orange, Plate 2, lightly overcast with Grenadine Pink, Plate 2. Reverse of petals—Light Buff, Plate 15, with outer edges of petal lightly overcast with Shrimp Pink, Plate 1, and lower half of the petal lightly overcast with Citron Yellow, Plate 16. General tonality from a distance—Light Salmon Orange, Plate 2, lightly overcast with Grenadine Pink, Plate 2.
- *Discoloration.*—General tonality at end of first day—Light Salmon Orange, Plate 2, overcast with Grenadine Pink, Plate 2. Second day—Light Salmon Orange, Plate 2, lightly overcast with Grenadine Pink, Plate 2. Third day—Light Salmon Orange, Plate 2, overcast with Orient Pink, Plate 2.

Petals:
- *Texture.*—Leathery; is not affected by wet or hot weather.
- *Appearance.*—Inside—satiny. Outside—shiny.
- *Form.*—Round; slightly notched.
- *Arrangement.*—Irregular.
- *Petaloids in center.*—Few; small.
- *Persistence.*—Drop off cleanly.
- *Fragrance.*—Strong. Nature—tea (average hybrid tea scent).
- *Lasting quality.*—On the plant—long. As cut flower—long.

GENITAL ORGANS

Stamens, anthers: Medium size; many.
- *Arrangement.*—Tucked in calyx.
- *Color.*—Orange Buff, Plate 3.

Stamens, filaments (threads): Long. Color—Pale Lemon Yellow, Plate 4.

Pollen: Color—Baryta Yellow, Plate 4.

Styles: Columnar; loosely separated; uneven length; medium length; thin.

Stigmas: Color—Pale Orange Yellow, Plate 3.

Ovaries: All enclosed in calyx.

Hips: None.

Seeds: None.

PLANT

Form: Bush.

Growth: Vigorous; upright.

Foliage: 5 to 7 leaflets.
- *Size.*—Large.
- *Quantity.*—Normal.
- *Color.*—New foliage: upper side—Light Hellebore Green, Plate 17, lightly overcast with Carmine, Plate 1; under side—Yellowish Oil Green, Plate 5, lightly overcast with Oxblood Red, Plate 1. Old foliage: upper side—Dark Cress Green, Plate 31; under side—Light Cress Green, Plate 31.
- *Shape.*—Oval pointed.
- *Texture.*—Upper side—glossy. Under side—smooth.
- *Ribs and veins.*—Ordinary.
- *Edge.*—Serrated (saw-toothed).
- *Serration.*—Both double and single; small.
- *Leaf stem.*—Color—Forest Green, Plate 31. Under side—prickles.
- *Stipules.*—Long; bearded.

*Disease resistance.*—Better than average resistance to mildew, black-spot and other common diseases, as well as more resistant to fumigant injury, as determined by comparison with other varieties grown at Newark, New York, under comparable cultural conditions.

Wood:

*New wood.*—Bark—smooth. Color—Parrot Green, Plate 6.

*Old wood.*—Bark—smooth. Color—Cress Green, Plate 31.

Thorns:

*Thorns.*—Quantity: on main stalks from base—many; on laterals from stalk—many. Form—narrow base; medium length; straight and sometimes hooked downward. Color when young—Napal Red, Plate 1. Position—irregular.

*Prickles.*—Quantity: on main stalks—none; on laterals—none.

*Short needles.*—Quantity: on main stalks—none; on laterals—none.

I claim:

A new and distinct variety of rose plant of the hybrid tea class, substantially as herein shown and described, characterized particularly as to novelty by the general similarity of color and form of its blooms to those of its parent variety "Ballet," combined with a more vigorous and healthier habit of growth of its plant and foliage, more freedom of growth especially under greenhouse conditions, and better resistance to disease and fumigant injury.

No references cited.